(12) United States Patent
Häfner et al.

(10) Patent No.: US 7,053,176 B1
(45) Date of Patent: May 30, 2006

(54) COMBINATION OF C1-INH AND LUNG SURFACTANT FOR THE TREATMENT OF RESPIRATORY DISORDERS

(75) Inventors: Dietrich Häfner, Constance (DE); Paul-Georg Germann, Lörrach (DE); Nils Ott, Hamburg (DE); Burkhard Vangerow, Ronnenberg (DE); Horst Rückoldt, Hannover (DE); Gernot Marx, Hannover (DE); Michael Cobas Meyer, Hannover (DE); Martin Leuwer, Wunstorf (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/088,294

(22) PCT Filed: Sep. 16, 1999

(86) PCT No.: PCT/EP99/06845

§ 371 (c)(1),
(2), (4) Date: Jul. 22, 2002

(87) PCT Pub. No.: WO01/19392

PCT Pub. Date: Mar. 22, 2001

(51) Int. Cl.
*A61K 45/00* (2006.01)

(52) U.S. Cl. .................. 530/300; 530/350; 436/13; 424/278.1

(58) Field of Classification Search ............... 530/300, 530/350; 436/13; 424/278.1, 178.1; 514/2
See application file for complete search history.

(56) References Cited

U.S. PATENT DOCUMENTS

| 5,891,844 A | 4/1999 | Häfner |
| 6,051,224 A * | 4/2000 | Strayer et al. ........... 424/131.1 |
| 6,129,934 A * | 10/2000 | Egan et al. ................ 424/557 |

FOREIGN PATENT DOCUMENTS

| DE | 32 29 179 | 2/1994 |
| EP | 0 055 041 A2 | 6/1982 |
| EP | 0 100 910 | 2/1984 |
| EP | 0 101 935 | 3/1984 |
| EP | 0 110 498 | 6/1984 |
| EP | 0 119 056 | 9/1984 |
| EP | 0 145 005 | 6/1985 |
| EP | 0 251 449 | 1/1988 |
| EP | 0 286 011 | 10/1988 |
| EP | 0 348 967 | 1/1990 |
| EP | 0 368 823 | 5/1990 |
| EP | 0 406 732 | 1/1991 |
| WO | WO 86/03408 | 6/1986 |
| WO | WO 87/06943 | 11/1987 |
| WO | WO 89/04326 | 5/1989 |
| WO | 90/07469 | 7/1990 |
| WO | WO 91/00871 | 1/1991 |
| WO | WO 91/18015 | 11/1991 |
| WO | 92/22320 | 12/1992 |
| WO | WO 95/32992 | 12/1995 |
| WO | 96/09831 A2 | 4/1996 |
| WO | 96/09831 A3 | 4/1996 |
| WO | WO 97/26863 | 7/1997 |
| WO | WO 97/35882 | 10/1997 |
| WO | 98/35683 | 8/1998 |
| WO | WO 98/49191 | 11/1998 |

OTHER PUBLICATIONS

Salvatierra, A. et al. (1997) C1-esterase inhibitor prevents early pulmonary dysfunction after lung transplantation in the dog. Am J Respir Crit Care Med. vol. 155, pp. 1147-1154.*
Gauthier, M. et al. (1997) Reactivation of C1-inhibitor polymers by denaturation and gel-filtration chromatography. Anal Biochem. vol. 248, pp. 228-233.*
Attchment 1 (2003) "Develops its surfactant as an inhalable aerosol that retains critical therapeutic properties" pp. 1-3.*
Attchment 2 (2003) "Meaning of liposome" p. 1.*
Vangerow, B., et al., "Effects of C1-Inhibitor and rSP-C surfactant on oxygenation and histology in rats with lavage-induced acute lung injury", 19th International Symposium on Intensive Care and Emergency Medicine, Brussels, Mar. 16-19, 1999, Poster Presentation.
Vangerow, B., et al'., "Effects of C1-Inhibitor and rSP-C surfactant on oxygenation and histology in rats with lavage-induced acute lung injury", *Critical Care, The Official Journal of the Critical Care Forum, Abstracts of Posters*, Editor: Jean-Louis Vincent, vol. 3, Supp. 1, Mar. 1999.

(Continued)

*Primary Examiner*—Jon Weber
*Assistant Examiner*—Samuel Wei Liu
(74) *Attorney, Agent, or Firm*—Nath & Associates PLLC; Joshua B. Goldberg; Sheldon M. McGee

(57) ABSTRACT

Pharmaceutical composition for the treatment of infant respiratory distress syndrome and acute lung injury (including adult respiratory distress syndrome) which contains C1 esterase inhibitor (C1-INH) and lung surfactant which comprises a lung surfactant protein.

8 Claims, 2 Drawing Sheets

OTHER PUBLICATIONS

Figure 1:
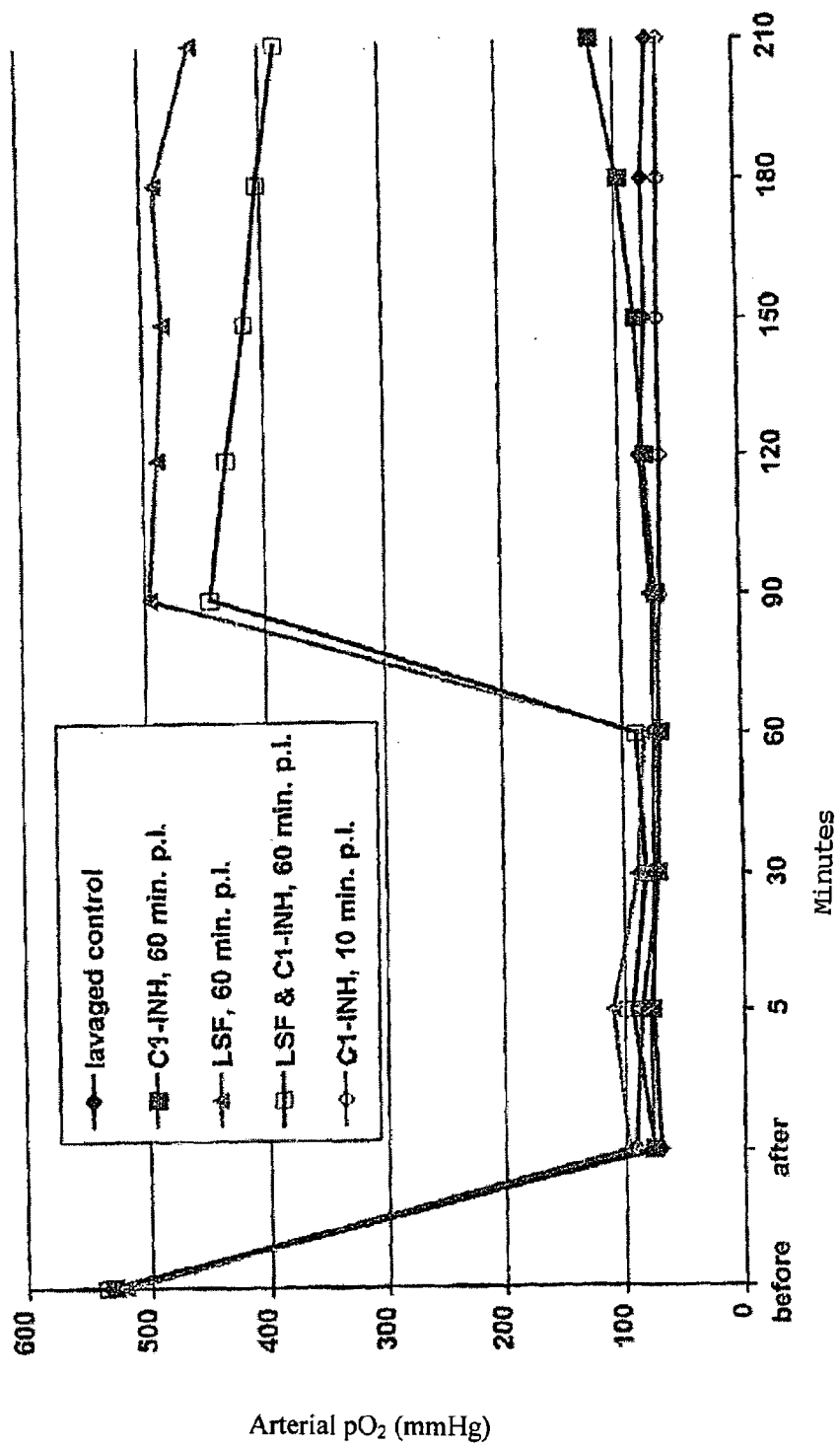

Possmayer, Fred, et al., "Calcium-Protein-Lipid Interactions in Pulmonary Surfactant". Prog. Resp. Res., vol. 18, pp. 112-120, 1984.

Maunder, Richard J., et al., "Clinical Risks Associated with the Adult Respiratory Distress Syndrome"; chapter 1 of Zapol, Lemaire eds., "Adult Respiratory Distress Syndrome", Marcel Dekker Inc., 1991.

Walmrath, D., et al., "Therapy in ARDS" *Intensivmedizin und Notfallmedizin*, vol. 36, No. 2, pp 104-125, (1999) XP-000856579.

Friedman, Lawrence S., et al., "Harrison's Principles of Internal Medicine, 14th Edition". 284, Peptic Ulcer and Related Disorders, 2000.

Schuster, Daniel P., "What is Acute Lung Injury? What is ARDS?". Chest 1995; 107; 1721-1726.

Lachmann, B., et al., "Exogenous surfactant therapy in adults". Atemw.-Lungenkrkh. 1993, 19: 581-591.

Gregory, T.J., et al., "Survanta® Supplementation in Patients with Acute Respiratory Syndrome (ARDS)". Am. J. Respir. Crit. Care Med., 1994, 149: A567.

Abraham, Edward, et al., "Liposomal prostaglandin $E_1$ in acute respiratory distress syndrome: A placebo-controlled, randomized, double-blind, multicenter clinical trial". Crit. Care Med. 1996, 24: 10-15.

Bernard, Gordon R., et al., "High-Dose Corticosteroids in Patients with the Adult Respiratory Distress Syndrome". N.Engl.J. Med. 1987, 317: 1565-1570.

Thiel, M., et al., "The role of polymorphonuclear leukocytes in the pathogenesis of the adult respiratory distress syndrome". Anaesthesist 1996, 45: 113-130. (English Abstract on 114).

Rice, Glenn C., et al., "Protection from endotoxic shock in mice by pharmacologic inhibition of phosphatidic acid". Proc. Natl. Acad. Sci. USA 1994, 91: 3857-3561.

Fisher, Charles J., et al., "Recombinant Human Interleukin 1 Receptor Antagonist in the Treatment of Patients With Sepsis Syndrome". JAMA 1994, 271: 1836-1843.

Goerke, Jon, "Lung Surfactant". J. Biochem. Biophys. Acta 1974, 344: 241-261.

King, R.J., et al., "Physiological Correlations . . . ". Am. J. Physiol. 1972, 223: 715-726.

Häfner, Dietrich, et al., "Effects of rSP-C Surfactant on Oxygenation and Histology in a Rat-Lung-Lavage Model of Acute Lung Injury". Am. J. Respir. Crit. Care Med. 1998, 158: 270-278.

Gommers, D., et al., "Bronchoalveolar lavage with a diluted surfactant suspension prior to surfactant instillation improves the effectiveness of surfactant therapy in experimental acute respiratory distress syndrome (ARDS)". Intensive Care Med. 1998, 24: 494-500.

* cited by examiner

COMBINATION OF C1-INH AND LUNG SURFACTANT FOR THE TREATMENT OF RESPIRATORY DISORDERS

This application is a 371 of PCT/EP99/06845 filed 16 Sep. 1999.

TECHNICAL FIELD

The invention relates to a novel combination and method for the treatment of disease conditions which are designated as Infant Respiratory Distress Syndrome (IRDS) and Acute Lung Injury (ALI) including Acute or Adult Respiratory Distress Syndrome (ARDS).

PRIOR ART

Adult Respiratory Distress Syndrome (ARDS) is a descriptive expression which is applied to a large number of acute, diffuse infiltrative pulmonary lesions of differing etiology if they are associated with a severe gas exchange disorder (in particular arterial hypoxemia). The expression ARDS is used because of the numerous clinical and pathological features common with Infant Respiratory Distress Syndrome (IRDS). If, in the case of IRDS, the lung surfactant deficiency caused by premature birth is predominant, then in the case of ARDS a lung surfactant malfunction is caused by the lung condition based on differing etiologies.

Triggering causes for ALI (Acute Lung Injury) including ARDS can, for example, be (cited in accordance with Harrison's Principles of Internal Medicine 10th Ed. 1983 McGraw-Hill Int. Book Comp.) diffuse pulmonary infections (e.g. due to viruses, bacteria, fungi), aspiration of, for example, gastric juice or in the case of near-drowning, inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass.

With a mortality of 50–60% (survey in Schuster Chest 1995, 107:1721–26), the prognoses of an ARDS patient are still to be designated as unfavourable.

The therapy of ARDS consists mainly in the earliest possible application of different forms of ventilation [e.g. PEEP (positive end-expiratory pressure), raising of the oxygen concentration of the respiratory air, SIMV (Synchronized Intermittent Mandatory Ventilation; Harrison's Principles of Internal Medicine 10th Ed 1983 McGraw-Hill Int. Book Comp)] up to extracorporeal membrane oxygenation (ECMO; Zapol and Lemaire Adult Respiratory Distress Syndrome, Marcel Dekker Inc. 1991).

The specific use of various ventilation techniques has only led to a small lowering of mortality and includes the risk of setting in motion a vicious circle. By ventilation with pressure and high $FiO_2$ (Fraction of Inspired Oxygen; proportion of oxygen in the respiratory air), the lungs themselves can be damaged and as a result of this even higher pressures and higher $FiO_2$ may be required in order to obtain an adequate oxygenation of the blood.

Nowadays different pharmacological approaches to the solution are also followed. These include lung surfactant substitution [survey, for example B. Lachmann, D. Gommers and E. P. Eijking: Exogenous surfactant therapy in adults, Atemw.-Lungenkrkh. 1993, 19:581–91; T. J. Gregory et al.: Survanta supplementation in patients with acute respiratory distress syndrome (ARDS), Am. J. Respir. Crit. Care Med. 1994, 149:A567] up to purely antiinflammatory therapy with, for example, prostaglandin $E_1$ ($PGE_1$; Abraham et al. Crit Care Med 1996, 24:10–15) or glucocorticosteroids (Bernard et al. N Engl J Med 1987, 317:1565–70). Although specific successes were achieved by the administration of lung surfactant (e.g. Walmrath et al. Am J Resp Crit Care Med 1996, 154:57–62), the purely antiinflammatory therapies led to few to no successes. This is in direct contrast to the pathological or histopathological findings in ARDS. Thus massive polymorphonuclear leucocyte infiltrations (survey, for example Thiel et al. Anesthesist 1996, 45:113–130) were found in the lungs and the lavage of patients with ARDS and a number of inflammatory mediators are detectable. In testing, $PGE_1$ is additionally present in a liposomal intravenous administration form (Abraham et al. Crit Care Med 1996, 24:10–15) as well as substances which aim at the inhibition of phosphatidic acids (e.g. Lisofylline; Rice et al. Proc Natl Acad Sci 1994, 91:3857–61) or recombinant human interleukin 1 (IL-1) receptor antagonists (Fisher et al. JAMA 1994, 271:1836–43). Both $PGE_1$ and the IL-1 receptor antagonist, however, are restricted in their therapeutic utility by side effects.

WO98/35683 indicates compositions for the treatment of ARDS and IRDS which contain N-(3,5-dichloropyrid-4-yl)-3-cyclopropylmethoxy-4-difluoromethoxybenzamide and lung surfactant. WO96/09831 indicates compositions for the treatment of ARDS and IRDS which contain a glucocorticosteroid and lung surfactant. EP-B-0 451 215 describes compositions for the administration of a pharmaceutical active compound via the lungs. These compositions include liposomes which contain a pharmaceutical active compound and a lung surfactant protein. EP-B-0 055 041 describes preparations for inhalation or infusion for the treatment of disorders of the respiratory organs, which contain an active compound against disorders of the respiratory organs and natural lung surfactant. Compositions for the treatment of ARDS and IRDS are not disclosed.

FIGURE LEGENDS

FIG. 1: Time course of $PaO_2$ [mean±SD] in the experimental groups. C1-INH: 200 U/kg b.w. C1-INH applied intraarterially. LSF: 25 mg/kg b.w. r-SP-C surfactant applied intratracheally.

Figure 2:
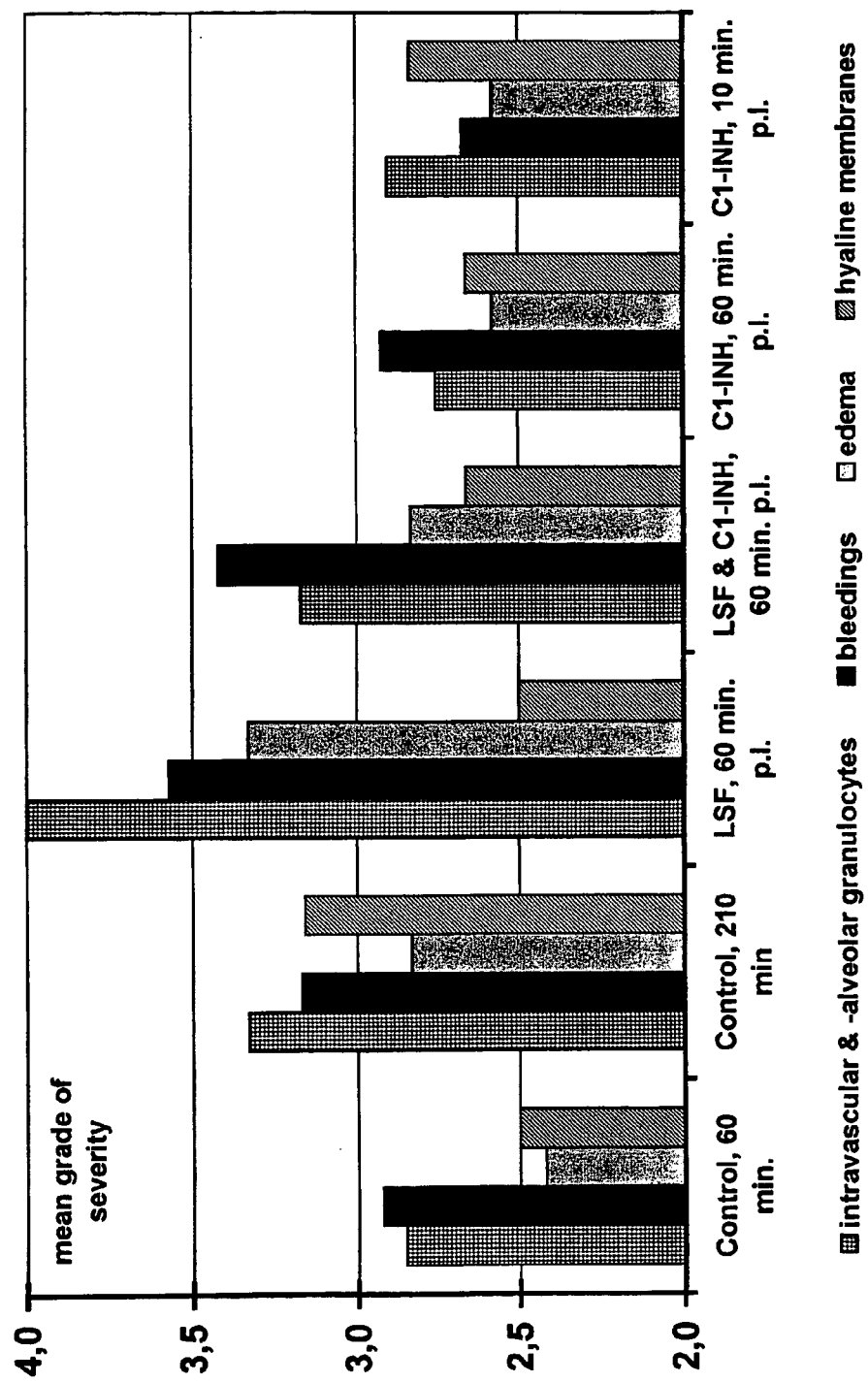

FIG. 2: Histopathological grading for hyaline membrane formation, neutrophil infiltration, bleedings and edema. Data are presented as mean severity grades of all six individual animals per group after coded histopathological evaluation. C1-INH: 200 U/kg b.w. C1-INH applied intraarterially. LSF: 25 mg/kg b.w. r-SP-C surfactant applied intratracheally.

DESCRIPTION OF THE INVENTION

It has now surprisingly been found that by the administration of a combination of C1-inhibitor and lung surfactant a synergistic effect can be achieved in the treatment of IRDS and ALI, including ARDS.

In a first aspect the invention relates to a pharmaceutical composition for the treatment of IRDS and ARDS comprising C1-inhibitor in combination with lung surfactant.

Further embodiments of the invention follow from the Patent claims.

In connection with the invention C1-inhibitor (hereinafter also referred to as C1-INH) refers to a protein, designated C1-inhibitor according to the ability to inhibit e.g. C1-esterase of the complement system and the bradykinin/kinin system. C1-inhibitor can be prepared by isolation from blood plasma according to methods known in the art. A process for production of C1-inhibitor for therapeutic purposes for example is disclosed in EP 0 101 935. A commercially available product comprising C1-inhibitor which may be mentioned is Berinert® HS [Centeon Pharma, Marburg (Lahn), Germany]. Berinert® is used in connection with the treatment of hereditary angioedema and congenital deficiency.

Lung surfactant is understood according to the invention as meaning the numerous known compositions and their modifications which have the function of natural lung surfactant. Natural lung surfactant has surface-active properties and reduces the surface tension in the alveolar region of the lungs. A simple and rapid quantitative in vitro assay to determine the surface activity of a surfactant preparation is e.g. the Wilhelmy balance [Goerke, J Biochim Biophys Acta, 344:241–261 (1974); King R. J. and Clements J. A., Am J Physiol 223:715–726 (1972)]. It gives an indication of surfactant quality in terms of the ability to approach a surface tension of near zero mN/m. It is performed by injecting a surfactant suspension at defined concentrations of phospholipids into a hydrous solution. The phospholipids spread to the air-liquid phase building a so-called monolayer. This monolayer reduces the surface tension of the hydrous solution. A platinum plate is carefully dipped into the solution. Now the force which pulls down the platinum plate can be measured with sensitive transducers. This force is proportional to the surface tension and depends on the dimensions of the platinum plate. An other method to describe the surface activity of surfactant preparations is the pulsating bubble surfactometer [Possmayer F., Yu S. and Weber M., Prog Resp Res, Ed.v. Wichert, Vol. 18:112–120 (1984)]. The activity of a surfactant preparation can also be assessed by an in vivo assay, for example, as described below in the section Pharmacology or in an assay as described by Häfner et al. (D. Häfner et al.: Effects of rSP-C surfactant on oxygenation and histology in a rat lung lavage model of acute lung injury. Am. J. Respir. Crit. Care Med. 1998, 158: 270–278). Measurement of lung compliance, blood gases and ventilator pressure will provide indices of activity.

Lung surfactant is to be understood according to the invention preferentially as compositions which will show activity in such an assay. Particular mention may be made of compositions which will show an activity in such an assay similar or greater to that of natural, in particular human, lung surfactant.

In particular lung surfactant compositions comprise phospholipids and inter alia can additionally contain lung surfactant proteins. Preferred phospholipids which may be mentioned in connection with the invention are dipalmitoylphosphatidylcholine (DPPC), palmitoyloleylphosphatidylglycerol (POPG) and/or phosphatidylglycerol (PG). Preferably the phospholipids are mixtures of dipalmitoylphosphatidylcholine (DPPC) and palmitoyloleylphosphatidylglycerol (POPG), in particular in a ratio from 7 to 3, to 3 to 7. Possible lung surfactant proteins are both the proteins obtained from natural sources, such as, for example, pulmonary lavage or extraction from amniotic fluid, and also synthetically or genetically engineered proteins. According to the invention, the lung surfactant proteins designated by SP-B and SP-C and their modified derivatives are particularly of interest. The amino acid sequences of these lung surfactant proteins, their isolation or preparation by genetic engineering are known (e.g. from WO-86/03408, EP-A-0 251, 449, WO-89/04326, WO-87/06943, WO-88/03170, EP-A-0 368 823 and EP-A-0 348 967). Modified derivatives of SP-C which differ from human SP-C by replacement of certain amino acids are disclosed for example in WO91/18015 and WO95/32992. Particular mention may be made of the SP-C derivatives disclosed in WO95/32992. According to the invention surfactant protein in particular refers to a recombinant SP-C derivative [hereinafter referred to as r-SP-C or r-SP-C (FF/I)] which differs from human SP-C by replacement of the two cysteines in position 4 and 5 by phenylalanine and replacement of the methionine in position 32 by isoleucine. The term lung surfactant protein as used herein also refers to mixtures of different lung surfactant proteins.

Further components which may be present in lung surfactant compositions are fatty acids, for example palmitic acid. The lung surfactant compositions may also contain electrolytes such as calcium, magnesium and/or sodium salts (for example calcium chloride, sodium chloride and/or sodium hydrogen carbonate), to set a favourable viscosity. The skilled worker will base his determination of the type and amount of individual constituents of the lung surfactant composition on the one hand on the known composition of natural pulmonary surfactant, and on the other hand on the numerous proposals in the prior art, such as for example, EP-A 0119056 and EP-A 0406732.

EP-B-0 100 910, EP-A-0 110 498, EP-B-0 119 056, EP-B-0 145 005 and EP-B-0 286 011 describes phospholipid compositions with and without lung surfactant proteins which are suitable, for example, as components of the preparations according to the invention.

Commercially available products which may be mentioned are Curosurf® (Serono, Pharma GmbH, Unterschleissheim), a highly purified natural surfactant from homogenized pigs' lungs, Survanta® (Abbott GmbH, Wiesbaden) and Alveofact® (Dr. Karl Thomae GmbH Biberach), both extracts of bovine lungs, and also Exosurf® (Deutsche Wellcome GmbH, Burgwedel), a synthetic phospholipid with auxiliaries.

Lung surfactant compositions in connection with the invention expediently contain 80 to 95% by weight of phospholipids, 0.2 to 5% by weight of surfactant protein, 2 to 15% by weight of fatty acids and 0 to 5% by weight of elektrolytes (of the dry mass).

Preferred lung surfactant compositions in connection with the invention contain 80 to 95% by weight of phospholipids, 0.5 to 3.0% by weight of surfactant protein, 3 to 15% by weight of fatty acids and 0 to 3% by weight of calcium chloride (of the dry mass).

Particularly preferred lung surfactant compositions in connection with the invention contain 80 to 95% by weight of phospholipids, 0.5 to 3.0% by weight of surfactant protein, 4 to 7% by weight of fatty acids, preferably palmitic acid and 1 to 3% by weight of calcium chloride (of the dry mass).

In connection with the invention combination means fixed, and free combinations, i.e. either C1-INH and lung surfactant are present together in one dosage unit, or C1-INH and lung surfactant, which are present in separate dosage units, are administered in direct succession or at a relatively large time interval; a relative large time interval means a time span up to a maximum of 24 hours. For use as separate dosage units, these are preferably made available together in one pack.

Separate dosage units for lung surfactant and C1-INH are prepared by procedures familiar to those skilled in the art, if appropriate using further suitable pharmaceutical auxiliaries. Preferably C1-INH is present in lyophilized form in connection with separate dosage units. A suitable product is known in the art under the trademark Berinert® HS. The preparation of a lung surfactant composition can be achieved by methods known to those skilled in the art, for example by incorporation of a surfactant protein into a phospholipid matrix, for example as described in WO95/32992. In connection with the invention, the lung surfactant compositions are made available preferably in lyophilized form and in particular in spray dried form. Lyophilized compositions are for example known from WO97/35882, WO95/32992, WO91/00871 and DE 3229179. WO97/26863 describes a process for the production of a lung surfactant composition in powder form by means of spray drying.

In connection with fixed combinations, the compositions according to the invention are prepared by procedures familiar to those skilled in the art, if appropriate using further suitable pharmaceutical auxiliaries. A powder form is obtained, for example, by directly mixing powdered forms of C1-INH and lung surfactant or by mixing liquid lung surfactant preparations, e.g. aqueous suspensions, with aqueous solutions of C1-INH and then lyophilizing and micronizing it. Alternatively, a solution of a lung surfactant and C1-INH can be lyophilized in a suitable solvent, such as, for example, isopropanol, and then micronized. Spray-drying of a mixture of an aqueous lung surfactant suspension and an aqueous C1-INH solution or a solution of a lung surfactant and C1-INH in suitable solvents, such as alcohols, (e.g. methanol, ethanol, 2-propanol) chloroform, dichloromethane, acetone and their mixtures, which optionally can additionally contain water may also leads to powdered preparations.

Pharmacology

Materials and Methods

Animal Preparation

The study protocol was reviewed and approved by the Laboratory Animal Care Committee at the district presidency of Freiburg, Germany in accordance with guidelines for ethical animal research. The study was performed with a total of 36 male Sprague Dawley rats (Harlan CBP, Zeist, The Netherlands), with a body weight (b.w.) of 242–264 g.

After induction of general anesthesia with halothane and nitrous oxide in oxygen an indwelling catheter was placed into one carotid artery. After intraperitoneal (i.p.) injection of pentobarbital (60 mg/kg b.w.) the rats were tracheotomized and a tube was secured into the trachea of each animal. Before mechanical ventilation was started the animals received an intramuscular (i.m.) injection of pancuronium bromide (2 mg/kg b.w.). The tracheal tubes of six animals were connected to a distributor and animals were ventilated simultaneously using a Servo 900 C ventilator (Siemens Elema, Solna, Sweden) at a respiratory rate of 30 breaths/min, a fraction of inspired oxygen ($FiO_2$) of 1.0, an inspiration/expiration ratio of 1:2, a peak inspiratory pressure (PIP) of 15 cm $H_2O$ and a positive end-expiratory pressure (PEEP) of 2 cm $H_2O$. Additional pentobarbital (i.p., 15 mg/kg b.w.) and pancuronium bromide (i.m., 2 mg/kg b.w.) were given when appropriate.

C1-Inhibitor

Pasteurized human C1-Inhibitor (Berinert® HS, Centeon, Germany) was resuspended with 9 ml physiological (0.9%) saline solution to achieve a concentration of 50 units (U)/ml. One unit is the amount of C1-INH present in 1 ml of normal human plasma (equal to 270 µg). Animals treated with C1-Inhibitor received 200 U/kg b.w. intraarterially.

Surfactant r-SP-C surfactant (Byk Gulden, Germany) contains 2% recombinant surfactant protein C (r-SP-C is an analog of human SP-C that has phenylalanine instead of two cysteines in positions 4 and 5 of the human SP-C sequence, and isoleucin in position 32 instead of methionine) embedded in a phospholipid matrix. It consists of dipalmitoylphosphatidylcholine and palmitoyloleoylphosphatidylglycerol at a ratio of 70:30 plus 5% (w/w) palmitic acid as related to phospholipids (PL). The r-SP-C surfactant was resuspended with physiological (0.9%) saline solution to achieve a concentration of 25 mg PL per ml. Surfactant was instilled intratracheally (i.t.) as bolus of 25 mg PL per kg body weight in a volume of 1.2 ml per animal. The r-SP-C surfactant was diluted with 0.9% saline solution to achieve the required concentration of 6.25 mg total PL per 1.2 ml.

Experimental Protocol

After instrumentation, blood samples were withdrawn from the arterial catheter for baseline determination of blood gases and C1-INH levels. Only animals with $PaO_2$ values of more than 480 mmHg were included in the experiments. Peak inspiration pressure (PIP) was raised to 28 cm $H_2O$ and PEEP to 8 cm $H_2O$ and the animals were subjected to multiple lung lavage (6–8 times) with 1 ml/30 g b.w. of isotonic saline solution. To avoid metabolic acidosis, 4 ml/kg b.w. of a glucose/$NaHCO_3$ solution (5 g glucose-monohydrate and 8.4 g $NaHCO_3$ dissolved in 100 ml 0.9% NaCl solution) were given by i.p. injection to each animal after lavage. Administration of glucose/$NaHCO_3$ was repeated if arterial $HCO_3^-$ decreased below 20 mmol/l during the experiment. Blood gases were determined at 5, 30, and 60 min after the last lavage using an ABL-500 blood gas analyzer (Radiometer, Copenhagen, Denmark). Only animals with $PaO_2$ values between 50 and 110 mmHg after the lavage procedure were included in the study.

Four experimental groups and two control groups were studied: In group 1 the animals were sacrificed one hour after the last lavage and in group 2 the animals were sacrificed at 210 min after the last lavage and these animals did not receive any treatment. In group 3 C1-INH (200 U/kg b.w.) was administered 60 minutes after the last lavage (p.l.). In group 4 the animals received 25 mg/kg b.w. r-SP-C surfactant at 60 min. p.l. In group 5 the animals were treated with C1-INH and r-SP-C surfactant at 60 min. p.l. In group 6 C1-Inhibitor was administered at 10 min. p.l. Subsequently, blood gases were determined 90, 120, 150, 180 and 210 min after the last lavage. During the whole experimental period PIP and PEEP were kept constant at 28 cm $H_2O$ and 8 cm $H_2O$, respectively. The animals were sacrificed at 210 minutes after the last lavage procedure.

Preparation of the Lungs

The lungs were carefully excised en bloc and fixed for 24 h in 8% phosphate-buffered formalin. Following fixation blocks of all lobes were sectioned and stained with haematoxylin and eosin (HE). After randomization and codification each section was examined under light microscopy. Hyaline membrane formation was assessed semiquantitatively according to the previously used technique (D. Häfner et al.: Effects of rSP-C surfactant on oxygenation and histology in a rat lung lavage model of acute lung injury. Am. J. Respir. Crit. Care Med. 1998, 158: 270–278). The severity of hyaline membrane formation was graded 0 to 4+(0, no hyaline membrane formation; 1+, occasional fields showing hyaline membrane formation in a low number (1–3) of membranes per viewed field (minimal); 2+, occasional fields showing hyaline membrane formation in an increased number (>3) of membranes per viewed field (mild); 3+, many but not all fields showing hyaline membrane formation (moderate); 4+, hyaline membrane formation in all fields examined (severe)). The distribution and severity of intraalveolar accumulation of PMNL's were graded semiquantitatively from 0 to 4+ comparable to the grading of hyaline membrane formation but with respect to the number of inflammatory cells and the location of these cells. The severity of intra-alveolar and perivascular hemorrhage were graded semiquantitatively using the same scale from 0 to 4+.

Sampling Procedure and C1-INH Assay

Blood samples for C1-INH determination were obtained at baseline and at 210 min. p.l. from the arterial catheter and placed into plastic tubes containing 3.8% sodium citrate. Plasma was obtained from blood samples centrifuged for 15 minutes at 2.500 g. All samples were stored at minus 700 Celsius. The activity of C1-Inhibitor was measured by an amidolytic method using an excess of C1-Esterase and $C_2H_5Co$-Lys(E-Cbo)-Gly-Arg-pNa as substrate (Berichrom C1-INH, Behring Diagnostics, Marburg, Germany). In this assay C1-INH inhibits cleavage of the chromogenic substrate by C1-Esterase. C1-INH activity of the samples was calculated from a reference curve prepared from human standard plasma.

Statistics

Results are presented as mean±standard deviation. Overall variations during the study protocol were analyzed using Kruskal-Wallis tests (nonparametric one-way analysis of variance). Subsequent comparisons between groups were analyzed using Wilcoxon tests and adjusted for multiple testing. All tests were two-tailed and a $p<0.05$ was considered statistically significant.

Results

Oxygenation

The arterial oxygen tension decreased from 530±14 mmHg (baseline) to 84±10 mmHg after the lavage procedure. No animal of the control group showed a spontaneous increase in arterial $pO_2$ during the experimental period. Arterial $pO_2$ increased significantly to 496±54 mmHg in group 4 (r-SP-C surfactant) and to 446±65 mmHg in group 5 (r-SP-C surfactant and C1-INH) at 30 minutes and remained high until sacrifice. $PaO_2$ values of animals treated with C1-Inhibitor only were comparable to controls with a tendency towards higher $paO_2$ values in animals receiving C1-INH at 60 minutes postlavage. FIG. 1 summarizes the effects of C1-INH and r-SP-C surfactant administration on arterial $pO_2$.

C1-Inhibitor

Baseline levels of C1-Inhibitor activity were 44±12% of human standard plasma. In the groups treated with C1-INH concentrate (group 3, 5 and 6), plasma levels increased to 210±41%. In the control groups (group 1 and 2) and animals treated with r-SP-C surfactant only (group 4) C1-INH activity remained at 36±14%.

Histopathological Evaluation

The gradings for the observed histopathological changes are presented in FIG. 2. In untreated controls only moderate hyaline membrane formation was present in the lungs at 60 minutes after the last lavage. The mean severity of hyaline membrane formation increased during the experiment from 2.50 at 60 minutes p.l. up to 3.16 at sacrifice. In addition to that, the grading for intravascular and intraalveolar granulocytes (margination of polymorphonuclear neutrophil leukocytes, PMNL), the intraalveolar bleedings and the formation of edema showed a similar time-dependant increase.

At 210 minutes after lavage, the formation of hyaline membranes was significantly reduced in group 3 (r-SP-C surfactant, see FIG. 2). The combination of r-SP-C surfactant with C1-INH (group 4) and C1-INH monotherapy 60 minutes after lavage (group 5) showed a comparable effect on the prevention of hyaline membrane formation to r-SP-C surfactant monotherapy (FIG. 2). CL-INH administration at 10 minutes after lavage (group 6) had only a minor effect on the prevention of hyaline membrane formation (FIG. 2). The intratracheal application of r-SP-C surfactant (group 3) lead to an increase in the histopathological gradings for intravascular and intraalveolar granulocytes, for intraalveolar bleedings and edema in comparison to the particular mean severity gradings of the 210 minutes control group (group 2) as shown in FIG. 2. The observed histopathological changes after r-SP-C surfactant monotherapy were less severe when r-SP-C surfactant was combined with CL-INH (FIG. 2). C1-Inhibitor monotherapy (group 5 and 6) reduced significantly the histopathological gradings for intravascular and intraalveolar granulocytes, for intraalveolar bleedings and edema formation (FIG. 2).

In the investigation of compositions according to the invention comprising C1-INH and lung surfactant in this model, it was found that the oxygenation and the histological changes improve synergistic in comparison with the sole administration of lung surfactant or C1-INH. Based on this unexpected result it can be concluded that by using a combination of C1-INH and lung surfactant the treatment of IRDS and ALI (including ARDS) can be shortened and the high mortality accompanying these syndromes can be reduced. Additionally it is possible either to save a portion of the very expensive LSF or to attain an enhanced effect of each of the components.

Commercial Utility

Adult Respiratory Distress Syndrome (ARDS) is a descriptive expression which is applied to a large number of acute, diffuse infiltrative pulmonary lesions of differing etiology if they are associated with a severe gas exchange disorder (in particular arterial hypoxemia). The expression ARDS is used because of the numerous clinical and pathological features common with Infant Respiratory Distress Syndrome (IRDS). If, in the case of IRDS, the lung surfactant deficiency caused by premature birth is predominant, then in the case of ARDS a lung surfactant malfunction is caused by the lung condition based on differing etiologies.

Triggering causes for ALI (Acute Lung Injury) including ARDS can, for example, be (cited in accordance with Harrison's Principles of Internal Medicine 10th Ed. 1983 McGraw-Hill Int. Book Comp.) diffuse pulmonary infections (e.g. due to viruses, bacteria, fungi), aspiration of, for example, gastric juice or in the case of near-drowning, inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass.

The compositions according to the invention are not only suitable for the treatment or prophylaxis of IRDS in premature babies and for the treatment or prophylaxis of ALI including ARDS in adults in particular in connection with multiple organ failure, but also for the treatment or prophylaxis of pneumonia, bronchitis, meconium aspiration syndrome, COPD (chronic obstructive pulmonary disease), asthma and cystic fibrosis.

The administration of the compositions according to the invention is accomplished according to methods known by those skilled in the art. Preferably the compositions according to the invention are dissolved or resuspended in a suitable solvent or resuspension medium for administration. This is particularly preferred in case of spray dried or lyophilized compositions. Preferably physiological saline solution is used as suitable resuspension medium. It may be advantageous to administer suspensions or solutions of the compositions according to the invention which contain from 6,25 to 100 mg phospholipids per ml suspension or solution. It is preferred to administer (per single administration) suspensions or solutions of the compositions according to the invention which contain from 6,25 to 200 mg phospholipids and from 1 to 600 IU mg C1-INH per kg body weight. In connection with pulmonary application it is preferred to administer from 1 to 60 IU C1-INH per kg body weight and in connection with systemic application it is preferred to administer from 6 to 600 IU C1-INH per kg body weight. Expediently the compositions are administered one to three times a day, for a period from one to seven days. In connection with systemic application of the C1-INH it is preferred to administer 6 to 600 IU C1-INH per kg body weight as bolus and 3 to 300 IU C1-INH per kg body weight per day as continuous infusion for the next three to four days.

In connection with fixed combinations the administration of the pharmaceutical composition is preferably accomplished by intratracheal installation (infusion or bolus) or by way of atomization.

In connection with free combinations the administration of the lung surfactant composition is preferably accomplished by intratracheal installation (infusion oder bolus) or by way of atomization and the administration of the C1-INH composition is preferably accomplished by injection or infusion. In case of separate dosage units, C1-INH and lung surfactant are administered in direct succession or at a relatively large time interval; a relative large time interval means a time span up to a maximum of 24 hours.

If desired, prior to administration of the compositions according to the invention a bronchoalveolar lavage, preferably with diluted lung surfactant suspension, can be carried out. Such a treatment is for example described by Gommers et al. [Bronchoalveolar lavage with a diluted surfactant suspension prior to surfactant instillation improves the effectiveness of surfactant therapy in experimental acute respiratory distress syndrome (ARDS), Intensive Care Med. 1998, 24:494–500] and in WO98/49191.

The invention furthermore relates to a method for the treatment of mammals, including humans, who are suffering from pneumonia, bronchitis, meconium aspiration syndrome, COPD (chronic obstructive pulmonary disease), asthma, cystic fibrosis, IRDS and/or ALI (including ARDS). The method is characterized in that a therapeutically active and pharmacologically effective and tolerable amount of the composition according to the invention is administered to the sick mammal.

The invention further relates to the use of a composition according to the invention for the production of medicaments for the treatment of pneumonia, bronchitis, meconium aspiration syndrome, COPD (chronic obstructive pulmonary disease), asthma, cystic fibrosis, IRDS and/or ALI (including ARDS).

Further subject of the invention is an article of manufacture comprising customary secondary packaging material and a pharmaceutical composition in a suitable primary packaging material (for example an ampoule or vial) contained within the secondary packaging material, wherein the pharmaceutical composition comprises C1-INH in combination with lung surfactant, optionally together with suitable pharmaceutical auxiliaries (for example saline solution for resuspension of active agents in case of powdered forms), and wherein the primary and/or secondary packaging material comprises a label or package insert which indicates that the pharmaceutical composition is useful for preventing or treating pneumonia, bronchitis, meconium aspiration syndrome, COPD (chronic obstructive pulmonary disease), asthma, cystic fibrosis, IRDS and/or ALI (including ARDS). The secondary packaging material, the primary packaging material and the label or package insert may comply with what is considered as standard for pharmaceutical compositions of this kind by those skilled in the art.

The invention claimed is:

1. A pharmaceutical composition comprising C1-inhibitor (C1-INH) and lung surfactant, wherein the lung surfactant comprises a lung surfactant protein.

2. A pharmaceutical composition as claimed in claim 1, wherein CI-INH and the lung surfactant are present in a fixed combination.

3. A pharmaceutical composition as claimed in claim 1, wherein the lung surfactant contains a mixture of phospholipids.

4. A pharmaceutical composition as claimed in claim 3, wherein the phospholipids are phospholipids which occur in natural lung surfactant.

5. A pharmaceutical composition as claimed in claim 1 wherein lung surfactant protein contains SP-B, SP-C, their modified derivatives, or mixtures of SP-B, SP-C and/or their modified derivatives, wherein said modified derivatives reduce the surface tension in the alveolar region of the lungs.

6. A pharmaceutical composition as claimed in claim 1, wherein the lung surfactant is obtained by pulmonary lavage.

7. A method of treating or preventing a disease or disorder selected from the group consisting of pneumonia, bronchitis, meconium aspiration syndrome, COPD (chronic obstructive pulmonary disease), asthma, cystic fibrosis, IRDS (Infant Respiratory Distress Syndrome), ALI (Acute Lung Injury), and ARDS (Adult Respiratory Distress Syndrome) in a patient, comprising administering to a patient in need thereof a therapeutically effective amount of the pharmaceutical composition as claimed in claim 1.

8. A commercial product comprising a primary packaging which contains a pharmaceutical composition, and secondary packaging, wherein the pharmaceutical composition comprises C1-INH and lung surfactant wherein the lung surfactant comprises a lung surfactant protein, and wherein the primary and/or secondary packaging comprises a label or package insert which indicates that the pharmaceutical composition is useful for preventing or treating one or more diseases or disorders selected from the group consisting of pneumonia, bronchitis, meconium aspiration syndrome, COPD (chronic obstructive pulmonary disease), asthma, cystic fibrosis, IRDS (Infant Respiratory Distress Syndrome), ALI (Acute Lung Injury), and ARDS (Adult Respiratory Distress Syndrome).

* * * * *

UNITED STATES PATENT AND TRADEMARK OFFICE
CERTIFICATE OF CORRECTION

| | |
|---|---|
| PATENT NO. | : 7,053,176 B1 |
| APPLICATION NO. | : 10/088294 |
| DATED | : May 30, 2006 |
| INVENTOR(S) | : Häfner et al. |

It is certified that error appears in the above-identified patent and that said Letters Patent is hereby corrected as shown below:

Claim 2, Column 10, Line 26, Please delete "CI-INH" and replace with -- C1-INH --

Claim 5, Column 10, Line 35, Please delete "wherein lung" and replace with -- wherein the lung --

Claim 8, Column 10, Lines 52-53, Please delete "and secondary" and replace with -- and a secondary --

Claim 8, Column 10, Line 54, Please delete "surfactant wherein" and replace with -- surfactant, wherein --

Signed and Sealed this

Twenty-second Day of August, 2006

JON W. DUDAS
*Director of the United States Patent and Trademark Office*